US00PP28693P3

(12) United States Plant Patent
Domen

(10) Patent No.: US PP28,693 P3
(45) Date of Patent: Nov. 28, 2017

(54) NORWAY SPRUCE TREE NAMED 'DOUGART12'

(50) Latin Name: ***Picea abies* (L.) H. Karst.**
Varietal Denomination: Dougart12

(71) Applicant: Norbert Artmeyer, Hörstel-Riesenbeck (DE)

(72) Inventor: Andy Domen, Wernhout (NL)

(73) Assignee: Norbert Artmeyer, Hörstel-Riesenbeck (DE)

( * ) Notice: Subject to any disclaimer, the term of this patent is extended or adjusted under 35 U.S.C. 154(b) by 73 days.

(21) Appl. No.: 14/756,885

(22) Filed: Oct. 26, 2015

(65) Prior Publication Data

US 2017/0118888 P1 Apr. 27, 2017

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

PUBLICATIONS

Upov Pluto Plant Variety Database Feb. 8, 2017 for *Picea* 'Dougart12' retrieved on Feb. 8, 2017, retrieved from the Internet at <https://www.3.wipo.int/pluto/user/en/index.jsp> one page.*

* cited by examiner

*Primary Examiner* — June Hwu
(74) *Attorney, Agent, or Firm* — The Webb Law Firm

(57) ABSTRACT

A new and distinct *Picea abies* plant that exhibits a compact and pyramidal

6 Drawing Sheets

Botanical classification: *Picea abies* (L.) H. Karst.
Varietal denomination: 'Dougart12'.

BACKGROUND OF THE INVENTION

The present invention comprises a new and distinct plant of *Picea abies* (L.) H. Karst. (Norway spruce tree) known by the varietal name 'Dougart12'. The new variety was discovered and selected from a group of seedlings in a cultivated area of an outdoor nursery bed in 2000 in Wernhout, The Netherlands. As such, its parental varieties are unknown. When compared to *Picea abies* variety 'Will's Zwerg' (unpatented), 'Dougart12' is more symmetrical in overall appearance, exhibits a faster growth rate, and has a smaller branch diameter. 'Dougart12' has been trial and field tested and has been found to retain its distinctive characteristics and remain true to type through successive propagations. The following characteristics distinguish the new variety from other *Picea abies* varieties:

1. Upright, pyramidal growth habit;
2. Compact (miniature) size;
3. Slow growth rate;
4. Short branches and internodes; and
5. Dark green-colored and short needles;

DESCRIPTION OF THE DRAWINGS

The accompanying photographic drawings illustrate the new variety, with the color being as nearly true as is possible with color illustrations of this type.

DESCRIPTION OF THE PLANT

Figure 1:
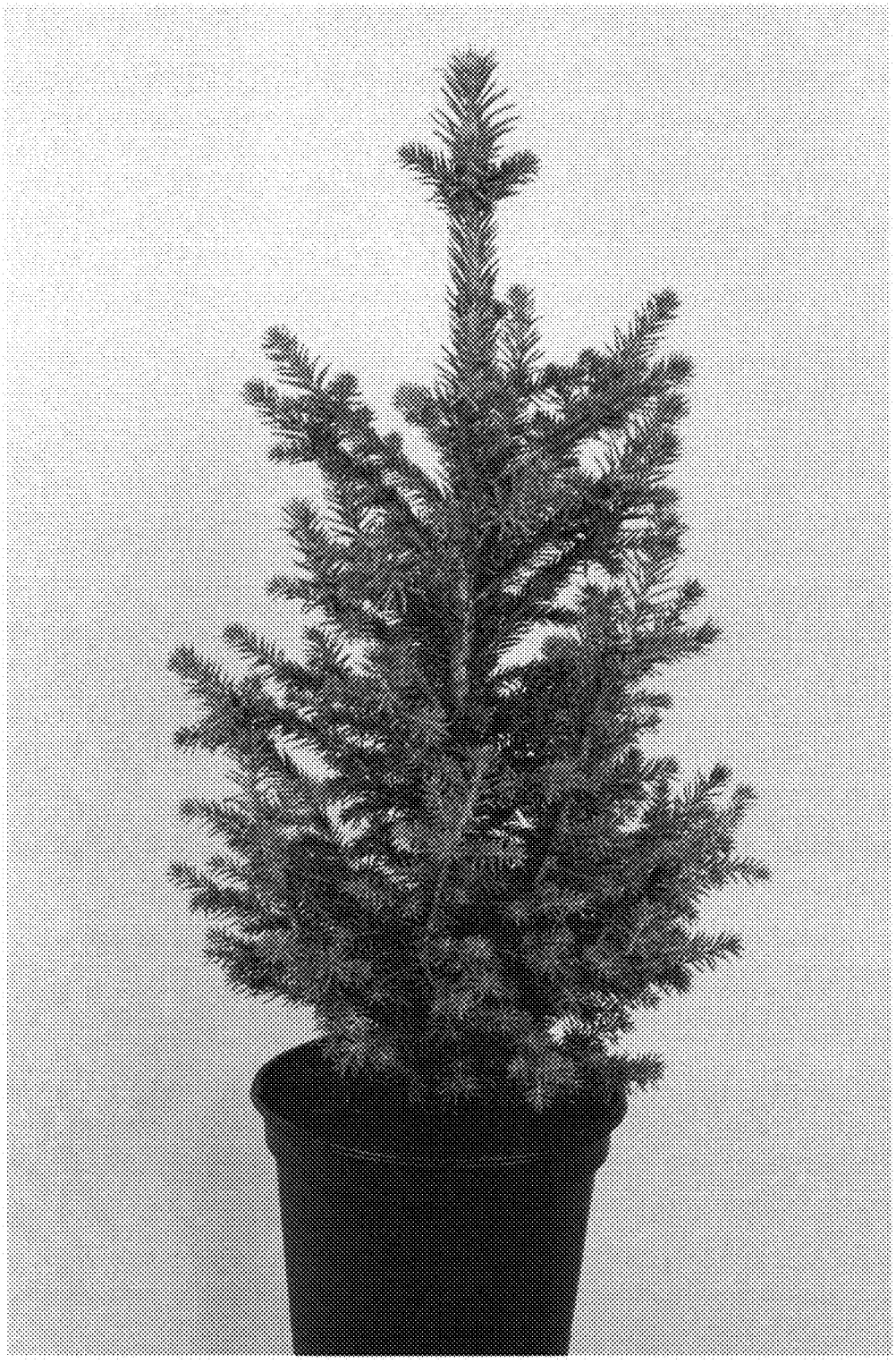
FIG. 1 shows a 3 year old plant of the new variety in a container.
Figure 2:
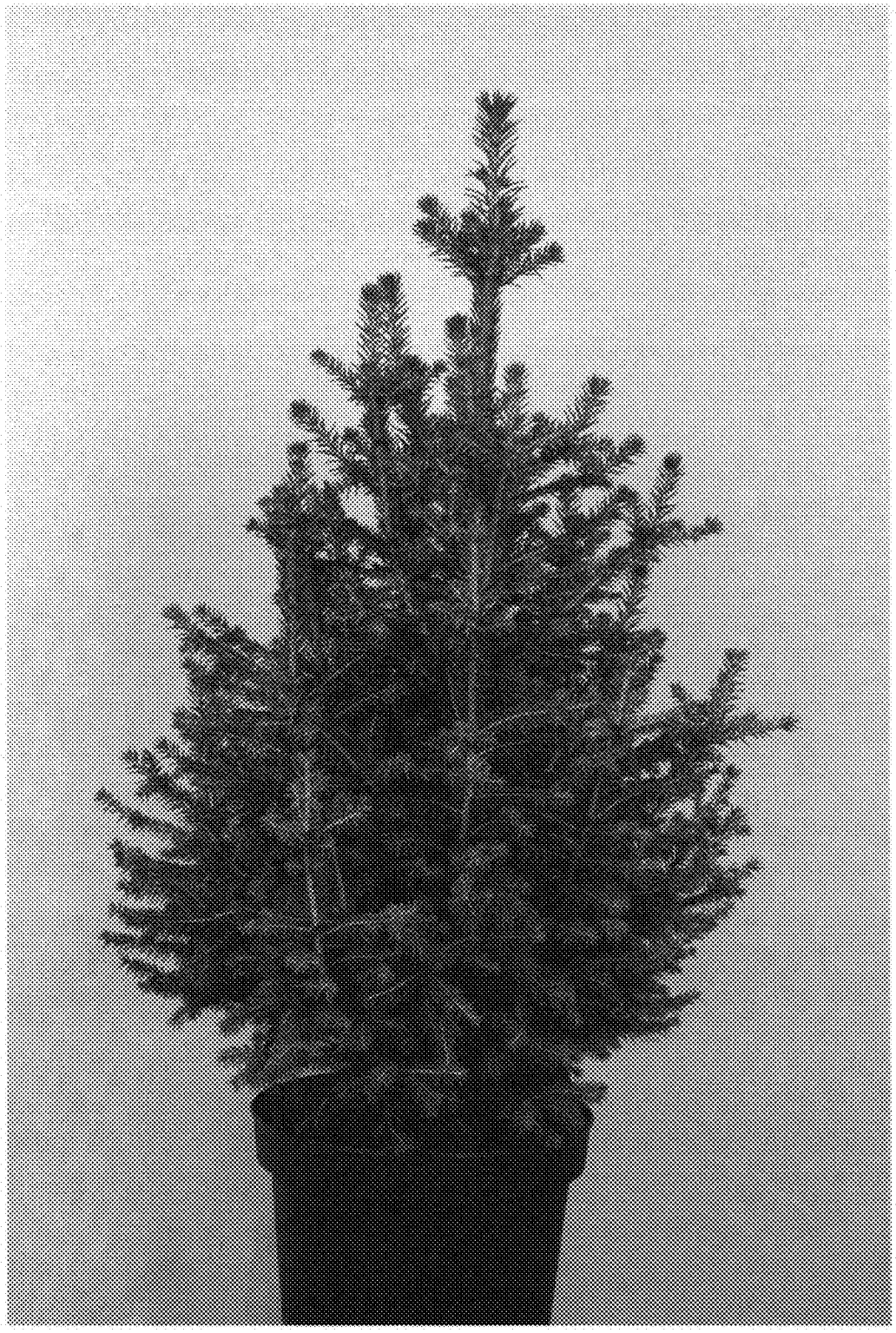
FIG. 2 shows a 4.5 year old plant of the new variety in a container.
Figure 3:
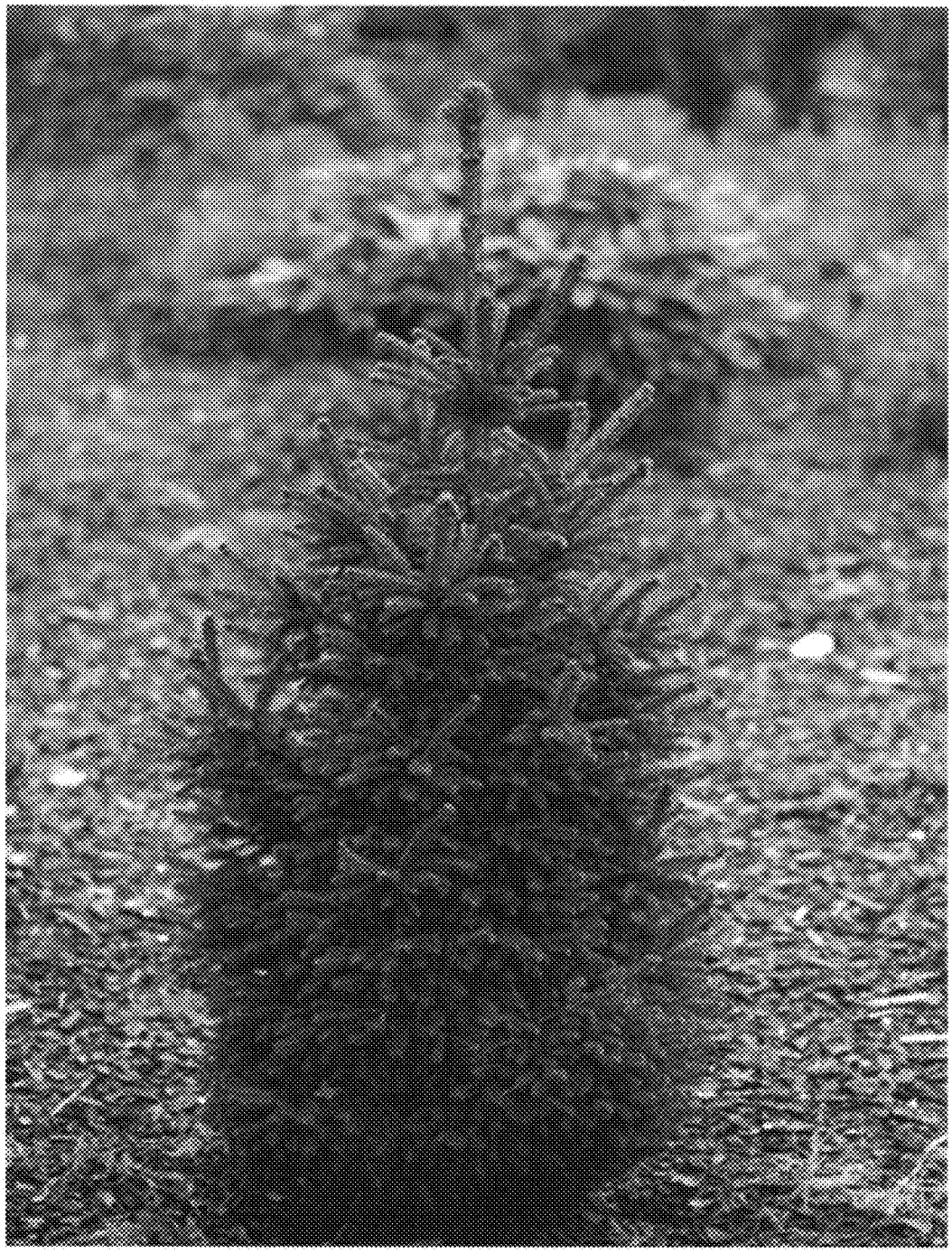
FIG. 3 shows an unpotted plant of the new variety.
Figure 4:
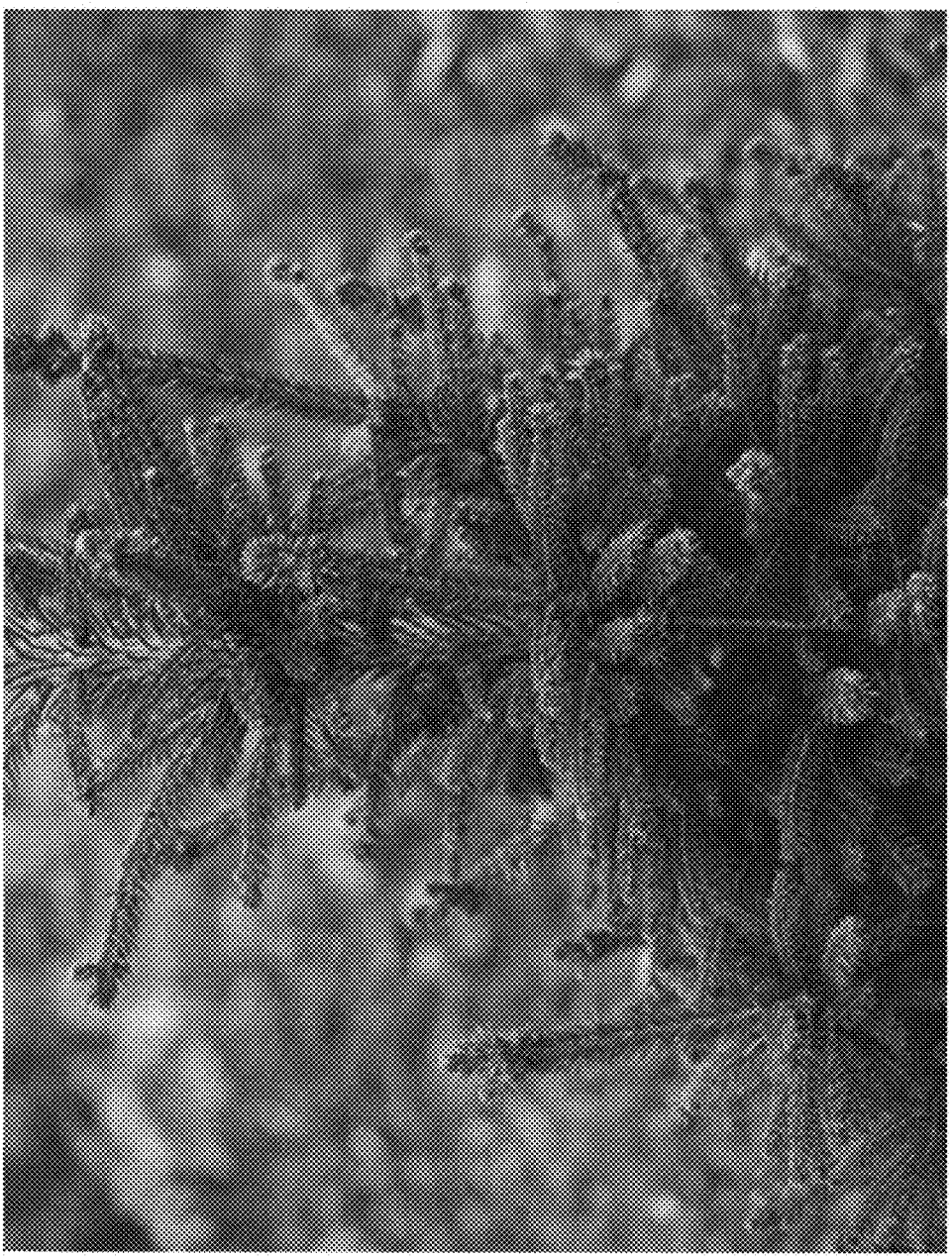
FIG. 4 shows a close-up view of the middle portion of the new variety.
Figure 5:
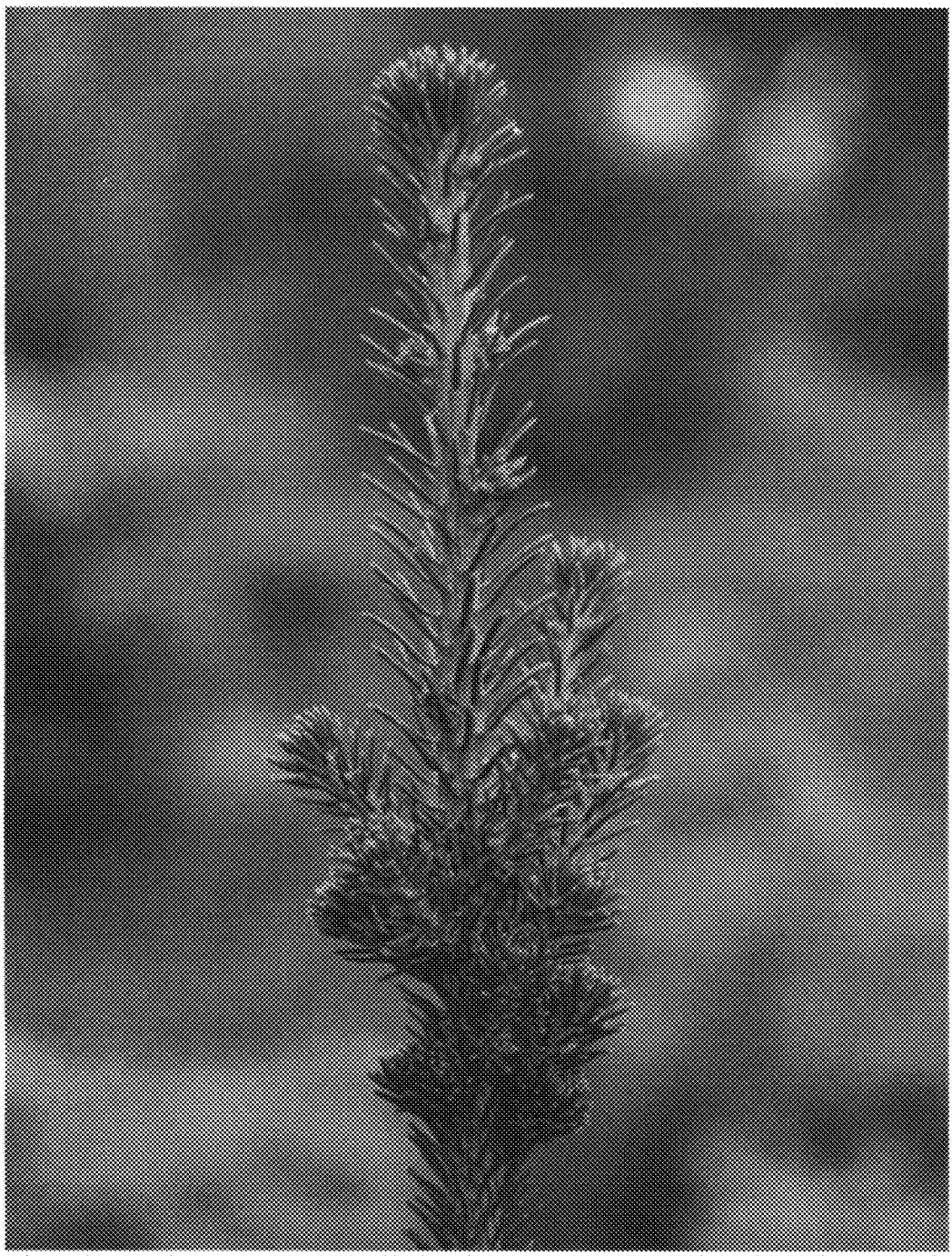
FIG. 5 shows a close-up view of the upmost tip of the main shoot of the new variety.
Figure 6:
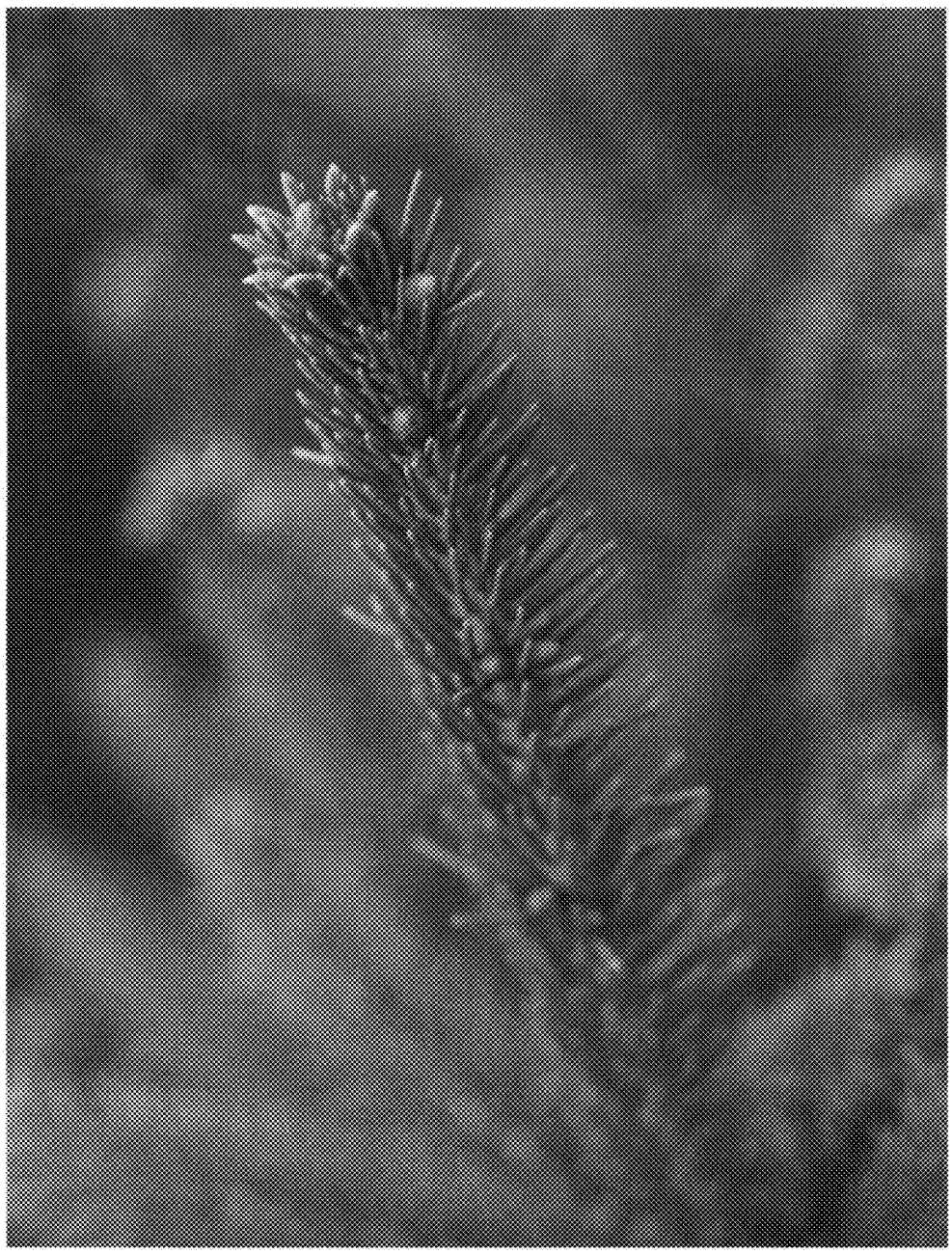
FIG. 6 shows a close-up view of a branch of the new variety.

The following detailed description sets forth the characteristics of the new cultivar. The data that defines these characteristics were collected by asexual reproductions performed via upright, upper branch shoot cuttings in 2008 carried out in Hörstel-Riesenbeck, Germany. Plants of the new variety were grown under natural daylight and outdoors with full sun. The color readings and measurements were primarily taken on 4-year-old plants grown in 7.5 liter containers. Color references are primarily to The 2007 R.H.S. Colour Chart of The Royal Horticultural Society of London, Fifth Edition.

PLANT

Plant type and use: Coniferous, evergreen tree for use as a Christmas tree.
Shape: Upright and conical/pyramidal.
Growth habit: Upright and conical; the main trunk grows from the base and has lateral branches.
Average growth rate: Between 15 to 20 cm per season.
Overall height: 200 cm at 10 years.
Overall diameter: 118 cm at 10 years.
Hardiness: Typical of *Picea abies* plants.

Cold temperature tolerance: Typical of *Picea abies* plants, to −25° C.

Time to produce a finished plant: 4 years, with a height of 60-70 cm.

Disease/pest resistance/susceptibility: None observed to date.

Trunk:

*Diameter.*—2.2 cm, measured at 20 cm in height from the ground.

*Color.*—Variations of Grey-Brown Group RHS 199D and Greyed-Green Group RHS 197B to 197D.

*Texture.*—Rough and scale-like.

Vegetative terminal bud:

*Average length.*—0.7 to 0.8 cm.

*Average width.*—0.4 to 0.5 cm.

*Shape.*—Ovate.

*Color.*—Grey-Brown Group RHS N199D.

*Time of beginning of terminal bud burst.*—Early to mid-season.

BRANCH DESCRIPTION

Average number:

*Main branches.*—1 trunk has 7 whorls and there are 4-5 main branches per whorl, averaging a total of 30 main branches when a plant is 50-60 cm high.

*Secondary branches.*—4-6 per main branch.

*Twigs.*—0-3 per secondary branch; low number of twigs overall.

Shape:

*Main branches.*—Rounded.

*Secondary branches.*—Rounded.

*Twigs.*—Rounded.

Color:

*Main branches.*—Greyed-Orange Group RHS 164B.

*Secondary branches.*—Greyed-Yellow Group RHS 162B.

*Twigs.*—Greyed-Yellow Group RHS 162B.

Diameter:

*Main branches.*—0.5 cm.

*Secondary branches.*—0.2 cm.

*Twigs.*—0.15 cm.

Length:

*Main branches.*—16-27 cm.

*Secondary branches.*—4-8 cm.

*Twigs.*—1-2 cm.

Surface description:

*Main branches.*—Rough and scale-like.

*Secondary branches.*—Rough and scale-like.

*Twigs.*—Rough and scale-like.

Branching description: Main branches extend upwardly from trunk at 30-45° angles.

Internode length:

*Between main and secondary branches.*—3-4 cm.

*Between twigs.*—Very short, with a low number of twigs.

NEEDLE DESCRIPTION

Needles:

*Arrangement.*—Alternate around the branches and twigs; imperfectly radial.

*Fragrance.*—Typical of *Picea abies* plants; spruce fragrance.

*Shape.*—Needle-shaped with weak curvature.

*Length.*—1.2 cm.

*Width.*—0.1 cm.

*Apex.*—Acute.

*Margin.*—Entire.

*Number per main branch.*—About 25 needles/3 cm.

*Number per secondary branch.*—About 40 needles/3 cm.

*Number per twig.*—About 20 needles/1 cm.

*Immature surface color.*—Green Group RHS 143A.

*Mature surface color.*—Green Group RHS 137A.

*Venation.*—None visible.

*Surface texture.*—Smooth.

*Resin glands.*—None visible.

CONE/SEED DESCRIPTION

Cone/seed description: None observed.

I claim:

1. A new and distinct variety of *Picea abies* plant named 'Dougart12', as is herein illustrated and described.

* * * * *